United States Patent
Rabizadeh et al.

(10) Patent No.: US 10,614,910 B2
(45) Date of Patent: Apr. 7, 2020

(54) SYSTEMS AND METHODS FOR COMPREHENSIVE ANALYSIS OF MOLECULAR PROFILES ACROSS MULTIPLE TUMOR AND GERMLINE EXOMES

(71) Applicants: Five3 Genomics, LLC, Santa Cruz, CA (US); NANTOMICS, LLC, Culver City, CA (US); NANT HOLDINGS IP, LLC, Culver City, CA (US)

(72) Inventors: Shahrooz Rabizadeh, Los Angeles, CA (US); John Zachary Sanborn, Santa Cruz, CA (US); Charles Joseph Vaske, Santa Cruz, CA (US); Stephen Charles Benz, Santa Cruz, CA (US); Patrick Soon-Shiong, Los Angeles, CA (US)

(73) Assignees: NANTOMICS, LLC, Culver City, CA (US); NANT HOLDINGS IP, LLC, Culver City, CA (US); FIVE3 GENOMICS, LLC, Santa Cruz, CA (US)

(*) Notice: Subject to any disclaimer, the term of this patent is extended or adjusted under 35 U.S.C. 154(b) by 603 days.

(21) Appl. No.: 14/726,930

(22) Filed: Jun. 1, 2015

(65) Prior Publication Data
US 2016/0026752 A1 Jan. 28, 2016

Related U.S. Application Data

(60) Provisional application No. 62/005,766, filed on May 30, 2014.

(51) Int. Cl.
*G16B 20/00* (2019.01)
*G16B 30/00* (2019.01)

(52) U.S. Cl.
CPC ............. *G16B 20/00* (2019.02); *G16B 30/00* (2019.02)

(58) Field of Classification Search
None
See application file for complete search history.

(56) References Cited

U.S. PATENT DOCUMENTS

| 2006/0293859 A1 | 12/2006 | Pipke et al. |
| 2009/0203050 A1 | 8/2009 | Bonavida et al. |
| 2012/0041683 A1 | 2/2012 | Vaske et al. |
| 2012/0059670 A1 | 3/2012 | Sanborn et al. |
| 2012/0066001 A1 | 3/2012 | Sanborn et al. |

FOREIGN PATENT DOCUMENTS

| JP | 2007-527220 | 9/2007 |
| WO | 2003065282 | 8/2003 |
| WO | 2011139345 | 11/2011 |
| WO | 2013062505 | 5/2013 |
| WO | 2014/012051 A1 | 1/2014 |
| WO | 2014/059036 A1 | 4/2014 |
| WO | 2014193982 | 12/2014 |
| WO | 2015/184439 A1 | 12/2015 |

OTHER PUBLICATIONS

Daves, Marla H., Susan G. Hilsenbeck, Ching C. Lau, and Tsz-Kwong Man. "Meta-analysis of multiple microarray datasets reveals a common gene signature of metastasis in solid tumors." BMC medical genomics 4, No. 1: 56 (Year: 2011).*
The Cancer Genome Atlas Network. Comprehensive molecular portraits of human breast tumors. Nature 2012, vol. 490, pp. 61-70 (Year: 2012).*
Hoadley et al. Multi-platform analysis of 12 cancer types reveals molecular classification within and across tissues of origin. Cell 2014, vol. 158, pp. 929-944 (Year: 2014).*
Ciriello et al., Emerging landscape of oncogenic signatures across human cancers, Nature Genetics, vol. 45, No. 10, Oct. 2013, pp. 1127-1135.
Jones et al., Personalized genomic analyses for cancer mutation discovery and interpretation, Science Translation Medicine, vol. 7 Issue 283, Apr. 15, 2015, pp. 1-11.
First Examination Report Received for Australian Patent Application Serial No. 2015266612 dated Feb. 10, 2017, 03 pp.
Examination Report received for Australian Patent Application Serial No. 2018201019 dated May 6, 2019, 02 Pages.
International Search Report and Written Opinion received for PCT Application Serial No. PCT/US2015033497 dated Oct. 27, 2015, 09 Pages.
Koboldt et al., "Comprehensive molecular portaits of human breast tumors", Cancer Genome Atlas Network, vol. 490, pp. 61-70, Oct. 4, 2012 (Apr. 10, 2012).
Notice of Allowance received for Korean Patent Application No. 1020167036845 dated Nov. 5, 2018, 1 Page.
Notice of Allowance received for Korean Patent Application Serial No. 1020197002709 dated May 20, 2019, 1 Page.
Second Examination report Received for Australian Patent Application Serial No. 2015266612 dated Jun. 1, 2017, 03 Pages.
Examination Report Received for Australian Patent Application Serial No. 2018201019 dated Dec. 3, 2019, 04 Pages.
Third Examination Report received for Australian Patent Application Serial No. 2015266612 dated Dec. 6, 2017, 03 Pages.
Daves, M. et al., Meta-analysis of multiple microarray datasets reveals a common gene signature of metastasis in solid tumors, BMC Medical Genomics, 2011, pp. 1-14, http://www.biomedcentral.com/1755-8794/4/56.

* cited by examiner

*Primary Examiner* — Olivia M. Wise
(74) *Attorney, Agent, or Firm* — Umberg Zipser LLP

(57) ABSTRACT

Omics patient data are analyzed using sequences or diff objects of tumor and matched normal tissue to identify patient and disease specific mutations, using transcriptomic data to identify expression levels of the mutated genes, and pathway analysis based on the so obtained omic data to identify specific pathway characteristics for the diseased tissue. Most notably, many different tumors have shared pathway characteristics, and identification of a pathway characteristic of a tumor may thus indicate effective treatment options ordinarily not considered when tumor analysis is based on anatomical tumor type only.

19 Claims, 7 Drawing Sheets

SYSTEMS AND METHODS FOR COMPREHENSIVE ANALYSIS OF MOLECULAR PROFILES ACROSS MULTIPLE TUMOR AND GERMLINE EXOMES

This application claims the benefit of priority to U.S. provisional application having Ser. No. 62/005,766, filed 30 May 2014, and which is incorporated by reference herein.

FIELD OF THE INVENTION

The field of the invention is computational omics, especially as it relates to analysis of molecular profiles across a large number of tumor and germline exomes from multiple patient and tumor samples.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

While the clinical world is familiar with genomic assays targeted to a limited number of mutations as a means to derive molecular insight to therapies, the power to deliver more comprehensive, non-assumptive, and stochastic molecular analysis is sorely needed to guide treatment decisions that are unbiased to traditional tissue-by-tissue anatomical assignment of therapeutics, or a priori assumptions that a few hundred DNA mutations are drivers of cancer. Indeed, most clinicians today are challenged by a deluge of rapidly advancing science with which it becomes increasingly difficult to keep pace. In this era of personalized medicine, there are nearly 800 drugs in development targeted against specific protein targets driving the growth of the tumor. This cognitive overload may have significant consequences in decision making in life-threatening diseases as complex as cancer.

Today the approach most widely used by oncologists to guide treatment selection of drugs that are targeted against altered proteins is to identify gene DNA mutations in tumor samples deploying panels of fewer than 500 "actionable" genes. Such actionable genes are typically identified from large-scale studies of various cancers (see e.g., Nature Genetics 45, 1127-1133 (2013)). All publications and applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Unfortunately, the current reliance on genotyping of tumor samples to drive treatment decisions is largely based on the assumption that identification of mutated DNA routinely translates downstream (from "DNA to protein expression") to an alteration in the underlying protein pathways that are targeted by the therapy to be selected, and these identified DNA mutations are thus nominated as clinically actionable. However, exclusive analysis of genetic mutations in tumor genomes fails to take into account whether or not the mutated genes are transcribed at all, whether changes in the genome are variants or disease-drivers, and/or what the functional context of such mutations are, and whether or not compensatory mechanisms exists in a cell affected by such mutation.

Therefore, analysis of selected mutations with disregard of the above drawbacks will likely lead to various false-positive, false negative, and non-relevant results that in turn may misdirect treatment of a patient. Therefore, there remains a need for improved systems and methods for comprehensive analysis of molecular profiles.

SUMMARY OF THE INVENTION

The inventive subject matter is drawn to systems and methods of omics analysis in which shared pathway characteristics are obtained from various distinct tumor samples. Most preferably, omics analysis includes analysis of tumor and matched normal tissue to identify patient and tumor specific changes, which is further refined using transcriptomics data. Based on such analysis, a treatment recommendation is then prepared that is typically independent of the anatomical tumor type but that takes into account a molecular signature characteristic of shared pathway characteristics.

In one aspect of the inventive subject matter, the inventors contemplate a method of identifying a molecular signature for a tumor cell that includes a step of using an analysis engine to receive a plurality of data sets from a respective plurality of patients, wherein at least two (or at least three, or at least five) of the plurality of patients are diagnosed with different tumors, and wherein each data set is representative of genomics information from tumor and matched normal cells. In another step, the analysis engine receives transcriptomics information for the at least two patients, and in yet another step, the analysis engine identifies shared pathway characteristics among the tumor cells of the at least two patients using the genomics information and the transcriptomics information. In a still further step, the analysis engine is then used to assign, on the basis of the shared pathway characteristics, a molecular signature to the tumor cells, wherein the molecular signature is assigned independently of an anatomical tumor type, and a patient record is then generated or updated using the molecular signature.

While not limiting to the inventive subject matter, it is generally contemplated that the data sets are in a BAMBAM format, a SAMBAM format, a FASTQ format, or a FASTA format, and it is typically preferred that the data sets are BAMBAM diff objects. Therefore, in further contemplated aspects, the data sets will preferably comprise mutation information, copy number information, insertion information, deletion information, orientation information and/or breakpoint information.

With respect to the genomics information it is contemplated that such information may be whole genome sequencing information or exome sequencing information, and that the transcriptomics information comprises information on transcription level and/or sequence information. Most typically, the transcriptomics information will cover at least 50% (or at least 80%) of all exomes in the genomics information from the tumor cells. Furthermore, it is contemplated that the transcriptomics information is used in the step of identifying to infer reduced or absence of function of a protein encoded by a mutated gene.

Therefore, the inventors contemplate that the shared pathway characteristics will include a constitutively activated pathway, a functionally impaired pathway, and a dysregulated pathway, and/or that the shared pathway characteristics may be characterized by a mutated non-functional protein, mutated dysfunctional protein, an overexpressed protein, or an under-expressed protein. In still further preferred aspects, the step of identifying is performed using PARADIGM or other pathway-centric method of analysis.

Additionally, it is contemplated that the molecular signature comprises information about one or more pathway elements, and especially drug identification and type of interaction with the one or more pathway elements. Therefore, it should be appreciated that the patient record may also include a treatment recommendation based on the molecular signature of the tumor cells (e.g., treatment recommendation for a first patient with a first tumor may be based on shared pathway characteristics with a second patient with a distinct second tumor).

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
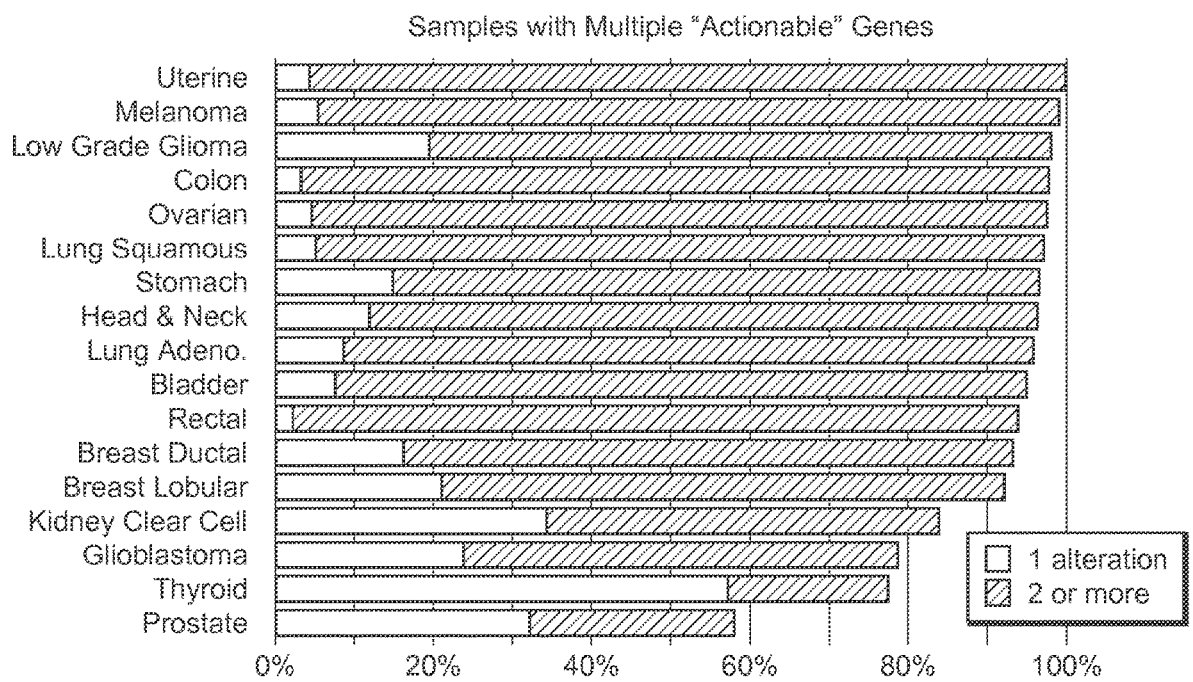
FIG. 1 is a graph illustrating frequency distribution of 'actionable genes' for selected tumors.

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems, and methods for improved omics analysis of various tumors. More specifically, the inventors discovered that omics data analysis can be significantly improved by first identifying patient and tumor relevant changes in the genome, typically via comparison of tumor and matched normal samples. Once such differences are ascertained, further transcriptomic data of the same patient are used to identify whether the changed sequences are expressed in the tumor. The so obtained patient data are then subjected to pathway analysis to identify pathway characteristics of the tumor, and particularly shared pathway characteristics of the tumor with various other types of tumors. As should be readily appreciated, shared pathway characteristics may be employed to inform treatment using one or more treatment modalities from anatomically unrelated tumors that would otherwise not have been identified. Viewed from a different perspective, different tumor types share pathway characteristics irrespective of the anatomical tumor type, and the knowledge of shared pathway characteristics with respective molecular signatures may identify drug treatment strategies that had not been appreciated for a particular tumor type.

Consequently, in one aspect of the inventive subject matter, the inventors contemplate a method of identifying a molecular signature for a tumor cell, and especially a molecular signature of a cell signaling pathway. Most typically, identification and analysis is performed using a fully integrated, cloud-based, supercomputer-driven, genomic, and transcriptomic analytic engine. It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

In especially preferred methods, an analysis engine receives a plurality of data sets from a respective plurality of patients, wherein at least two of the plurality of patients are diagnosed with different tumors, and wherein each data set is representative of genomics information from tumor and matched normal cells. In a further step, the analysis engine receives transcriptomics information for the at least two patients and identifies shared pathway characteristics among the tumor cells of the at least two patients using the genomics information and the transcriptomics information (of course, it should be noted that shared pathway characteristics may also be identified only for a single patient sample while pathway characteristics of other tumors may be obtained from a pathway database). In yet another step, the analysis engine is then used to assign, on the basis of the shared pathway characteristics, a molecular signature to the tumor cells, wherein the molecular signature is assigned independently (i.e., in an agnostic manner) of an anatomical tumor type. In a still further step, a patient record may be generated or updated using the molecular signature.

With respect to the data sets from the plurality of patients it is contemplated that the type of data sets may vary considerably and that numerous types of data sets are deemed suitable for use herein. Therefore, data sets may include unprocessed or processed data sets, and exemplary data sets include those having BAMBAM format, SAMBAM format, FASTQ format, or FASTA format. However, it is especially preferred that the data sets are provided in BAMBAM format or as BAMBAM diff objects (see e.g., US2012/0059670A1 and US2012/0066001A1). Therefore, and viewed from another perspective, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

It should also be noted that the data sets may be streamed from a data set generating device (e.g., sequencer, qPCR machine, etc.) or provided from a data base storing the data sets. For example, suitable data sets may be derived from a BAM server (e.g., as described in US2012/0059670A1 and US2012/0066001A1) and/or a pathway analysis engine (e.g., as described in WO2011/139345A2 and WO2013/062505A1). Such is particularly true where the data sets from a tumor and matched normal sample are not derived from the patient. Thus, at least some of the data sets may be independently stored and provided, and analysis may be performed on a newly obtained patient sample (e.g., within one week of obtaining patient tissue samples) using data sets from the patient's tumor and matched normal sample and previously stored tumor and matched normal sample not derived from the patient.

With further respect to the data sets it is noted that the data sets from all tumors are in a format that allows ready comparison without further conversion and/or processing. Thus, the data sets will preferably comprise mutation information, methylation status information, copy number information, insertion/deletion information, orientation information, and/or breakpoint information specific to the tumor and the patient. It is still further contemplated that the data set is representative of at least a portion of the entire genome, and most typically the whole genome. Therefore, the data sets are preferably prepared form whole genome sequencing covering the entire genome (or at least 50%, or at least 70%, or at least 90% of the entire genome). Alternatively, exome sequencing is also contemplated, and in most cases it is contemplated that at least 50%, more typically at least 70, and most typically at least 90% of the entire exome is sequenced.

Moreover, and with respect to the origin of the data sets it should be appreciated that numerous non-patient tumor data are used. Therefore, it is contemplated that for data sets other than a patient data set will be derived from at least two different tumors, and more preferably from at least three, or at least five different tumor types to identify shared pathway characteristics. Data sets from different tumor types can be obtained from different patient samples as such samples are available (e.g., from a hospital, clinical trial, epidemiological study, etc.) and/or can be provided from previously acquired analyses or data. For example, the TCGA provides a good sample of well-characterized omic information useful to prepare data sets suitable for use herein and Table 1 below exemplarily illustrates data used in the present analysis.

| Tissue | Subtype | N | Age | Sex M | Sex F | Tumor Grade G1 | G2 | G3 | G4 | GX | GB | ? | Median Survival (months) |
|---|---|---|---|---|---|---|---|---|---|---|---|---|---|
| Breast | ER– | 16 | 50.3 (58.9 ) | 0 | 16 | 0 | 0 | 0 | 0 | 0 | 0 | 16 | 26.04 |
| Lobular | ER+ | 148 | 62.0 (61.9) | 0 | 146 | 0 | 0 | 0 | 0 | 0 | 0 | 148 | 146.48 |
| Lung Squamous | | 366 | 66.5 (67.6) | 287 | 99 | 0 | 0 | 0 | 0 | 0 | 0 | 366 | 46.76 |
| Rectal | | 96 | 67.7 (66.0) | 53 | 40 | 0 | 0 | 0 | 0 | 0 | 0 | 90 | 51.98 |
| Breast Ductal | ER– | 225 | 56.3 (56.7) | 0 | 225 | 0 | 0 | 0 | 0 | 0 | 0 | 225 | 100.70 |
| | ER+ | 516 | 59.5 (58.2) | 9 | 507 | 0 | 0 | 0 | 0 | 0 | 0 | 516 | 113.62 |
| Glioblastoma | | 354 | 60.8 (60.1) | 222 | 132 | 0 | 0 | 0 | 0 | 0 | 0 | 354 | 13.94 |
| Stomach | MSI | 55 | 69.0 (68.6) | 46 | 42 | 0 | 30 | 55 | 0 | 0 | 0 | 0 | 26.47 |
| | MS3 | 160 | 67.0 (65.9) | 105 | 55 | 0 | 54 | 99 | 0 | 4 | 0 | 0 | 72.23 |
| AML | | 4 | 60.1 (50.2) | 3 | 1 | 0 | 0 | 0 | 0 | 0 | 0 | 4 | 47.05 |
| Low Grade Glioma | | 138 | 41.1 (42.8) | 72 | 66 | 0 | 68 | 70 | 0 | 0 | 0 | 0 | 78.21 |
| Head & Neck | HPV– | 246 | 62.4 (62.7) | 168 | 78 | 26 | 159 | 55 | 0 | 0 | 0 | 0 | 47.97 |
| | HPV+ | 56 | 59.4 (69.6) | 46 | 8 | 1 | 31 | 19 | 2 | 3 | 0 | 0 | 52.31 |
| Bladder | | 118 | 68.8 (67.1) | 56 | 32 | 0 | 0 | 0 | 0 | 0 | 0 | 118 | 19.50 |
| Uterine | | 299 | 63.6 (64.0) | 0 | 299 | 0 | 0 | 0 | 0 | 0 | 0 | 299 | NA |
| Prostate | | 178 | 61.3 (60.8) | 178 | 0 | 0 | 0 | 0 | 0 | 0 | 0 | 178 | NA |
| Lung Adeno. | | 369 | 66.9 (66.7) | 171 | 195 | 0 | 0 | 0 | 0 | 0 | 0 | 369 | 40.00 |
| Colon | MSS | 144 | 68.2 (66.8) | 62 | 62 | 0 | 0 | 0 | 0 | 0 | 0 | 144 | NA |
| | MSI | 76 | 73.1 (69.0) | 33 | 48 | 0 | 0 | 0 | 0 | 0 | 0 | 70 | NA |
| Thyroid | | 419 | 46.9 (47.6) | 104 | 315 | 0 | 0 | 0 | 0 | 0 | 0 | 419 | NA |
| Kidney Clear Cell | | 325 | 60.4 (60.4) | 209 | 116 | 0 | 142 | 126 | 47 | 2 | 0 | 8 | 90.45 |
| Kidney Chromophobe | | 60 | 48.3 (60.0) | 29 | 21 | 0 | 0 | 0 | 0 | 0 | 0 | 50 | NA |
| Ovarian | | 338 | 59.5 (60.4) | 0 | 336 | 3 | 37 | 285 | 0 | 8 | 1 | 2 | 43.66 |
| Melanoma | | 301 | 66.8 (67.3) | 192 | 109 | 0 | 0 | 0 | 0 | 0 | 0 | 301 | 98.40 |
| Pancreatic | | 4 | ? | ? | ? | 0 | 0 | 0 | 0 | 0 | 0 | 4 | NA |
| Total | | 5052 | | | | | | | | | | | |

With reference to the TCGA data it was further observed that different tumor types had multiple mutations in multiple genes. As such, it is apparent that simple targeting of an individual druggable target is in most circumstances not a viable option. Indeed, FIG. 1 exemplarily illustrates the predicament for conventional singular molecular diagnostics where various tumor types are shown with their respective numerical distribution of potentially actionable genes. As is readily apparent from FIG. 1, there was a multitude of actionable genes, not just single mutation, in almost all tumors. Thus, it should be appreciated that the analysis and treatment of a tumor requires consideration of more than one changed gene. In addition, it has previously not yet been appreciated that not all of the mutated genes are indeed expressed, and with that may or may not lead to actionable or druggable protein targets as is exemplarily depicted in FIG. 2.

Figure 2:
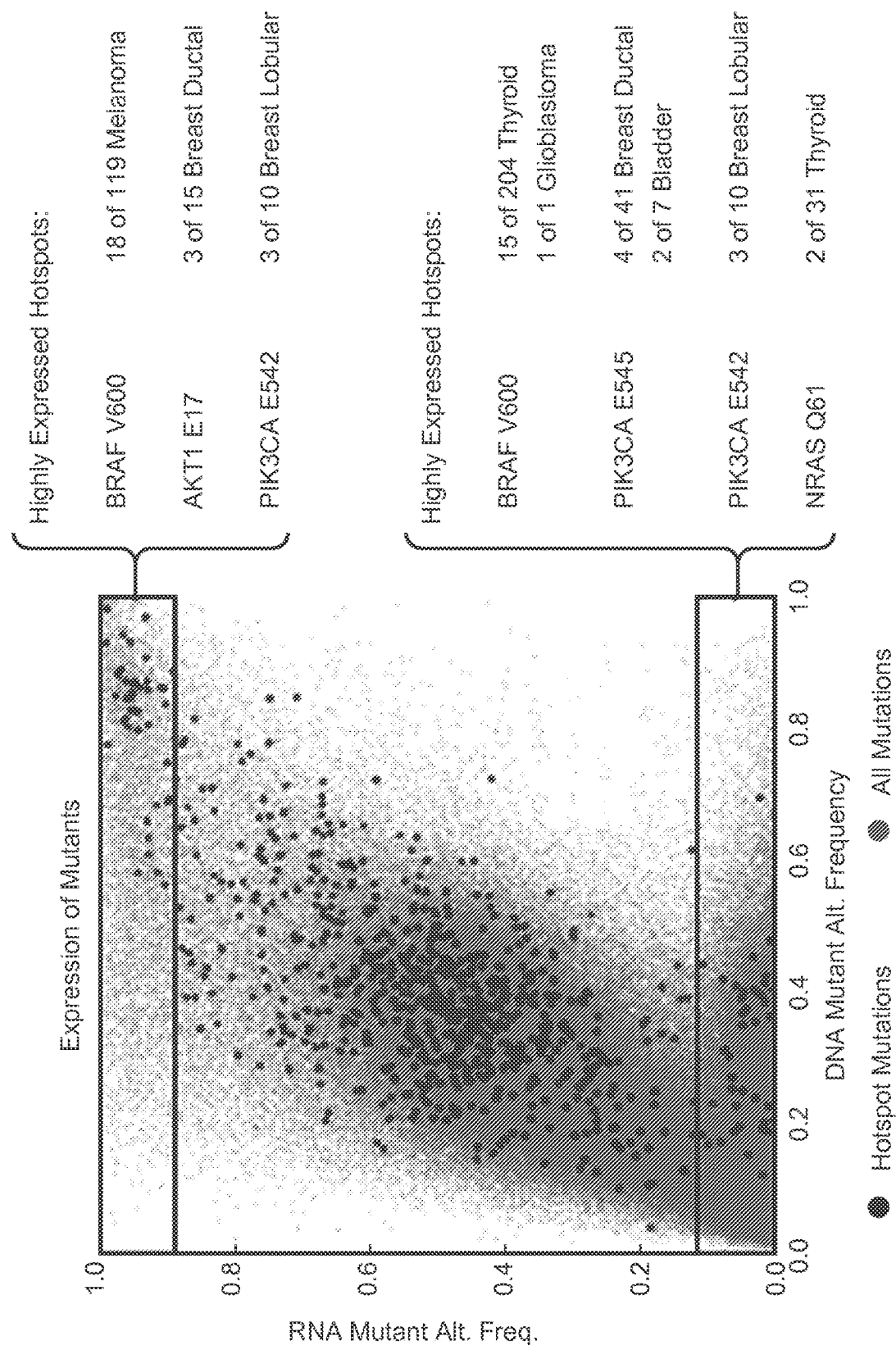
FIG. 2 is a graph correlating RNA expression levels of mutated genomic DNA for selected tumors.

As can be taken from FIG. 2, selected mutations in certain tumors were not or only weakly expressed (i.e., transcribed into RNA, see lower box). Consequently, pharmaceutical intervention targeting such mutant proteins (e.g., targeting BRAF V600 in glioblastoma) are not expected to impact the tumor in a significant manner. Conversely, certain other mutated proteins will provide an attractive target due to their very high rate of expression (e.g., by targeting BRAF V600 in melanoma). Thus, it should be appreciated that the same mutated protein may be a suitable target in some cancers or patients and an entirely unsuitable target in others. Viewed from a different perspective, genomics information without consideration of transcriptomics data will lack detail needed to guide treatment decisions.

In particularly preferred aspects, transcription information is obtained to cover at least 50%, or at least 70, or at least 80, or at least 90% of all exomes in the genomics information from the tumor cells. Thus, it is contemplated that transcripts of a tumor cell or tissue may also be analyzed for their quantity (and optionally also for sequence information to identify RNA editing and/or RNA splicing). Such analysis may include threshold values that are typically user defined as further described in copending US provisional application with the Ser. No. 62/162,530, filed 15 May 2015.

In addition to the lack of consideration of transcriptomics data, the functional impact of a mutation within a cell signaling network has not been appreciated in most of heretofore known systems and methods, especially where multiple mutations are present in multiple genes associated with a tumor. To overcome such shortcoming, the inventors used the patient and tumor specific mutation information and associated expression levels in an analysis of cell signaling pathways to thereby obtain information on pathway usage and compensation where a pathway function was compromised. Therefore, it is noted that the transcriptomics information is preferably used to infer reduced or absence of function of a protein encoded by a mutated gene, and with that influence on a particular pathway.

While various pathway analytical tools are known in the art, the inventors especially contemplate use of dynamic pathway maps in which pathways are expressed as probabilistic pathway model. For example, pathway analyses may be performed using PARADIGM, as described in WO2011/139345, WO2013/062505, WO2014/059036, or WO2014/193982, using the data sets and transcriptomics information to so arrive at the particular pathways usage of a specific tumor. As will be readily appreciated, where multiple data sets from multiple patients having distinct tumors as employed, the analysis engine will be able to identify for each tumor particular pathway characteristics with a molecular signature of the tumor cells. For example, the analysis engine may identify shared pathway characteristics among multiple tumor types where such shared characteristics may include a constitutively activated pathway, a functionally impaired pathway, and a dysregulated pathway. Such shared pathway may be characterized or due to a variety of factors and exemplary factors leading to a particular pathway characteristic include a mutated non-functional protein, mutated dysfunctional protein, an overexpressed protein, or an underexpressed protein in a pathway, etc. Of course, it should be noted that at least some of the pathway characteristics may be previously determined and stored in a data base or that at least some of the pathway characteristics may also be determined de novo. Therefore, it should be recognized that new patient data may be compared against already obtained data from a database.

Figure 4:
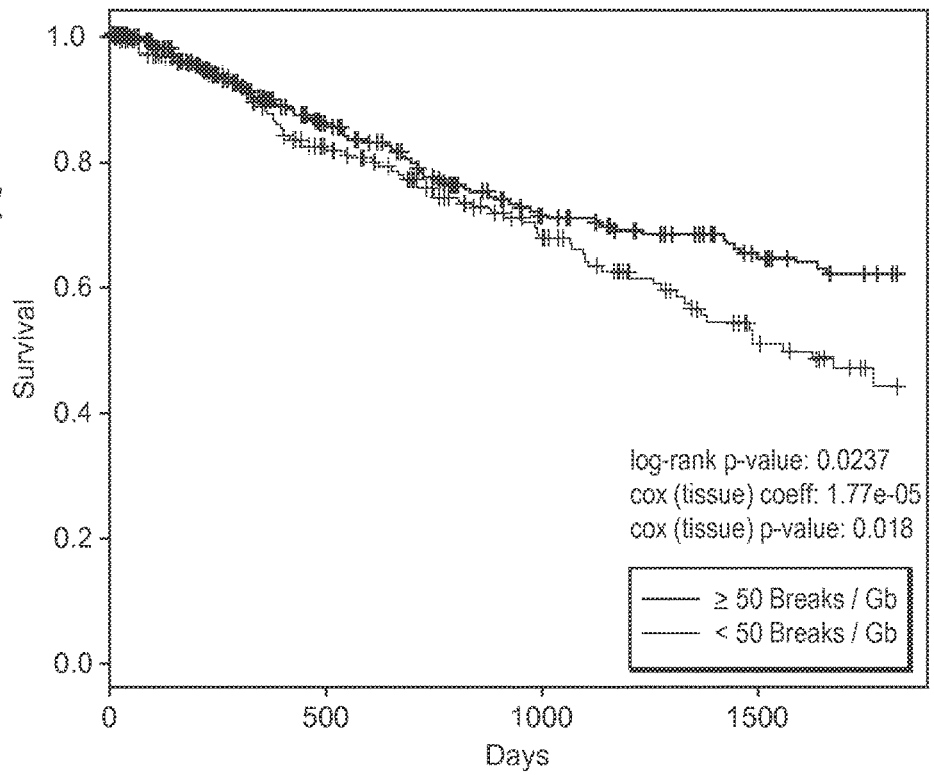
FIG. 4 is a an exemplary graph depicting survival times as a function of genomic rearrangements.
Figure 3:
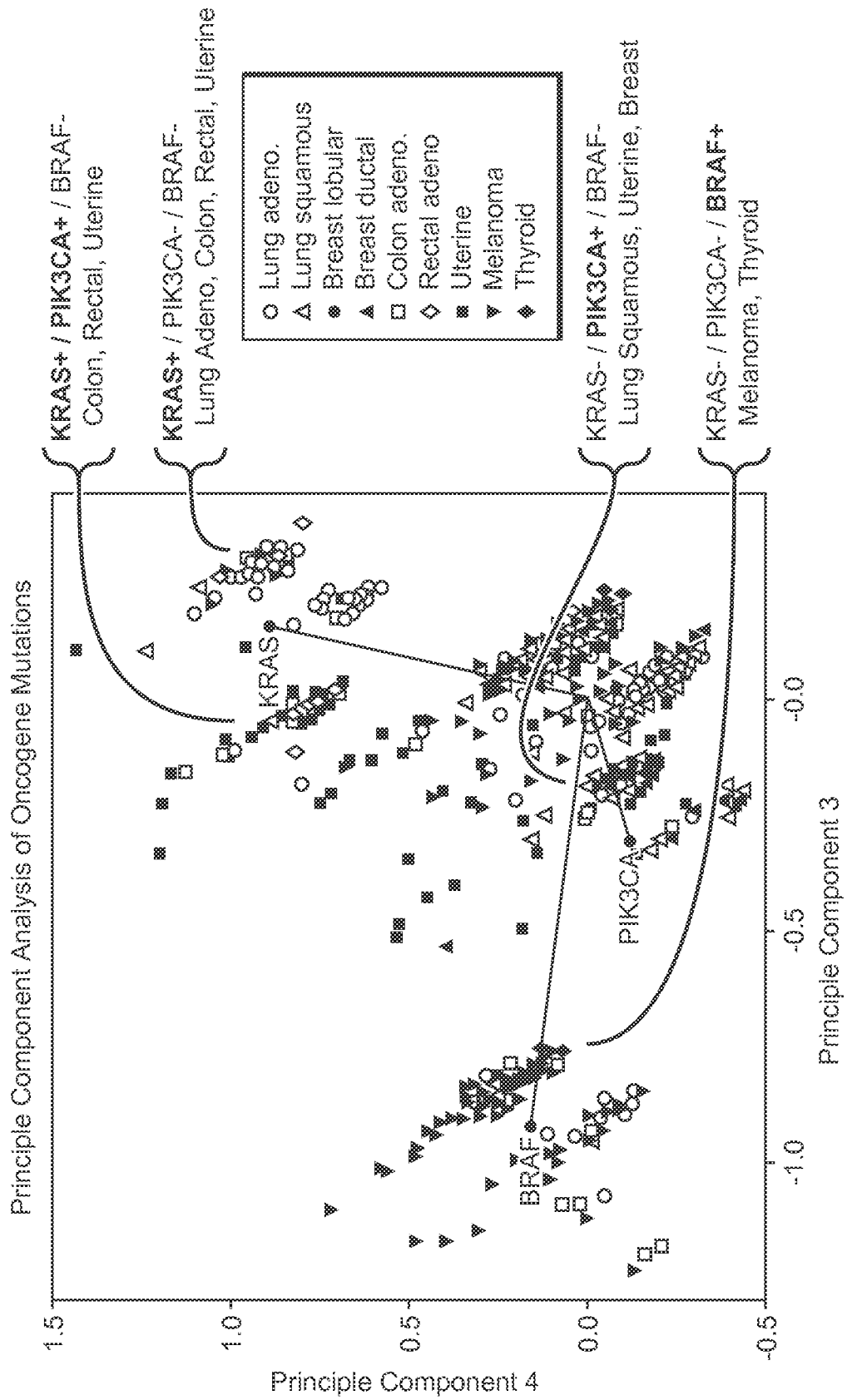
FIG. 3 is an exemplary graph depicting principal component analysis for selected oncogenes in selected tumors.
Figure 5:
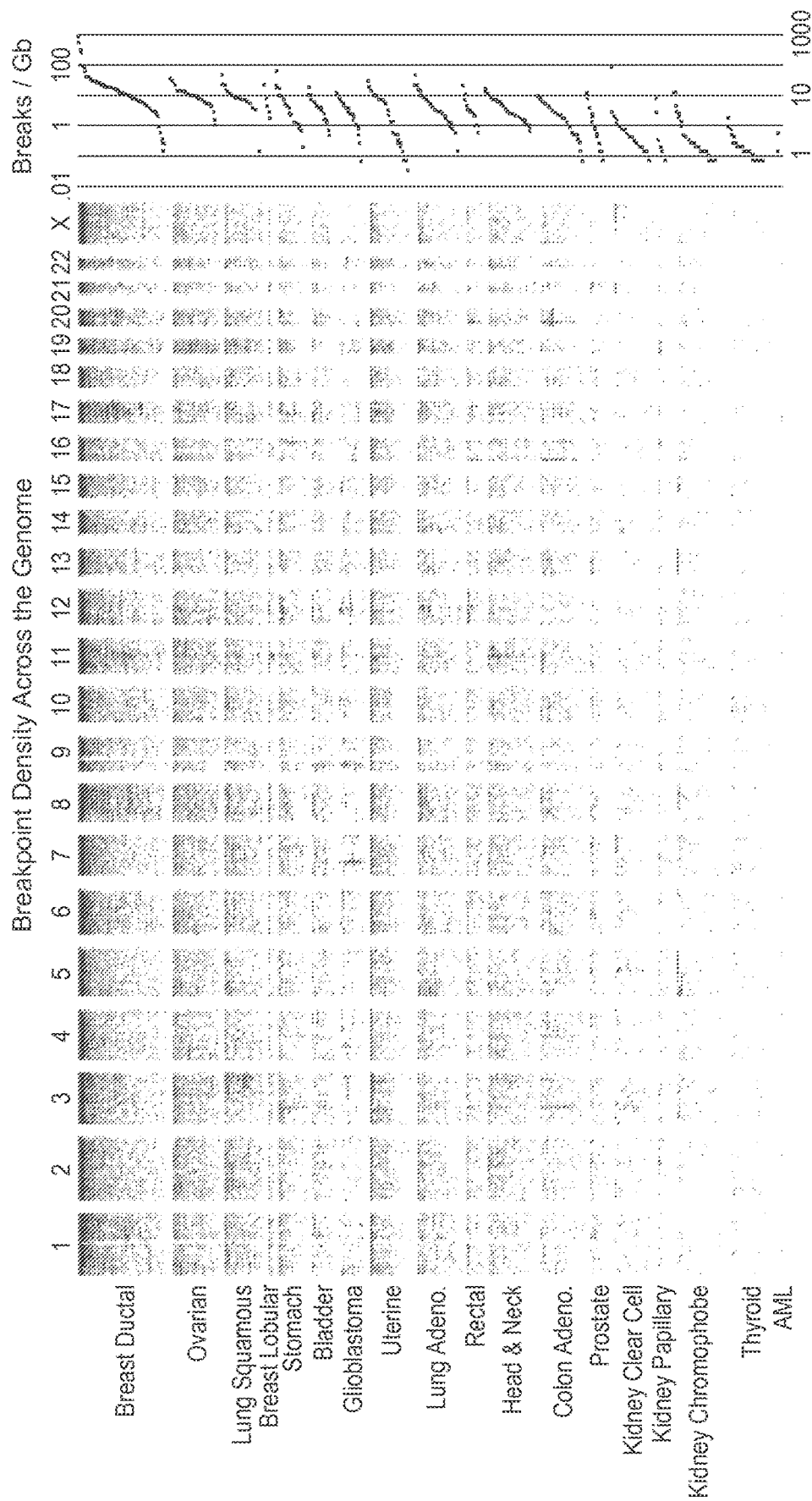
FIG. 5 is a chart depicting an exemplary breakpoint analysis for selected tumors.

Among other benefits of integrated genomics, transcriptomics, and pathway analysis for multiple tumor types of multiple patients, it should be appreciated various subsequent analyses are now possible to group or classify certain molecular events into otherwise not observable categories. For example, as is illustrated in FIG. 3, a principal component analysis of various expressed mutated oncogenes from different tumors can be performed to so associate a plurality of specific mutations with a plurality of different tumors. Likewise, breakpoint analysis over different tumors can be associated with prognostic outcome as exemplarily shown in FIG. 4, or breakpoint frequency and distribution can be associated with different tumors as exemplarily shown in FIG. 5.

Figure 6:
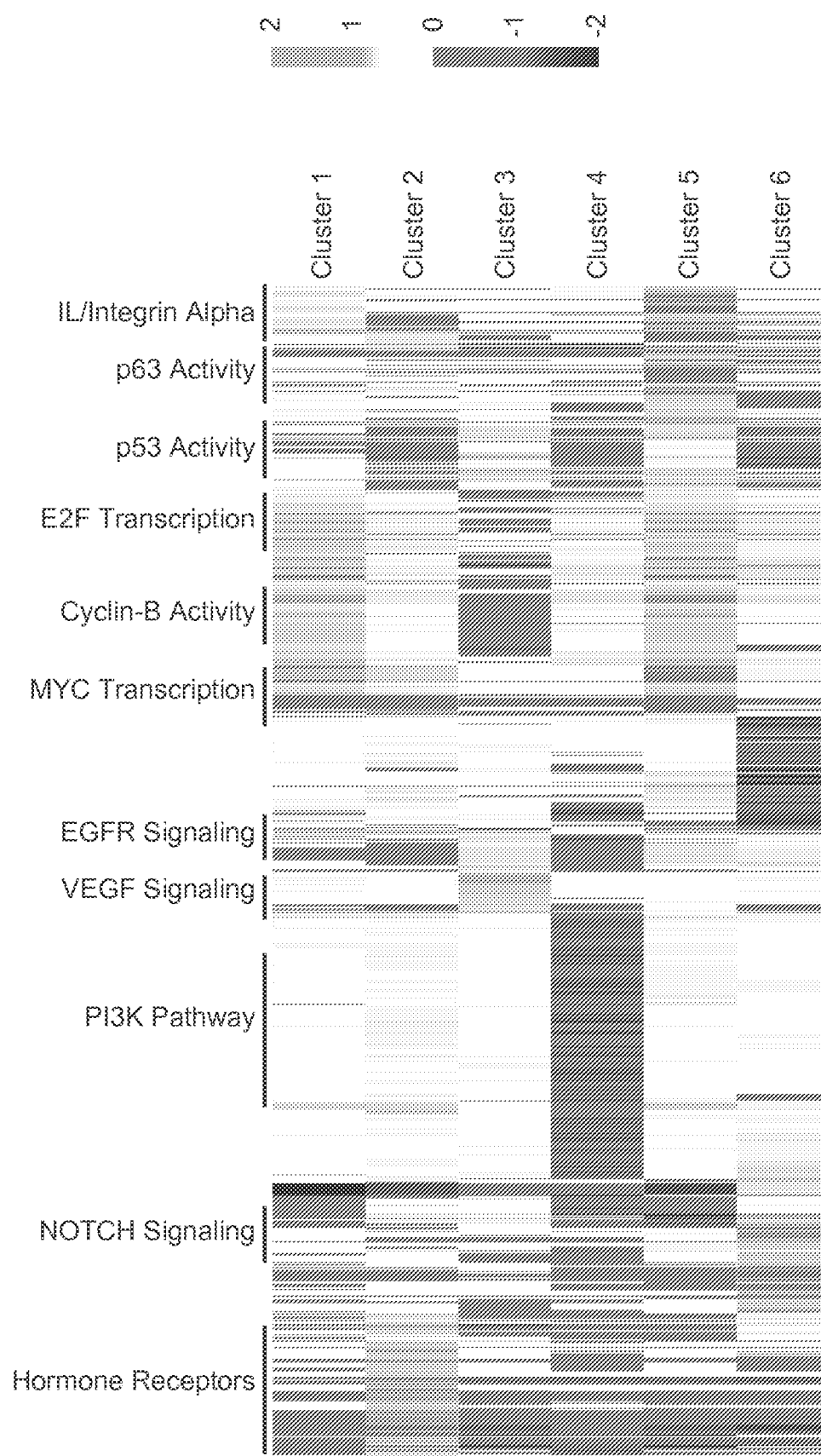
FIG. 6 is a graph depicting pathway activity clusters based on core pathways that are over- or under-activated.

Most notably, and as exemplarily shown in FIG. 6, pathway analysis on the basis of genomics and transcriptomics information may serve to identify certain shared molecular signatures common to a variety of different tumors. Thus, it should be recognized that a tumor may be classified as belonging to a class of tumors that are characterized by specific shared pathway characteristics. With further reference to FIG. 6, it is noted that the tumors of Table 1 together with genomics and transcriptomics information were stratified into six distinct classes independent of anatomical location. Here, common classes for different tumors were defined by activation or inhibition of selected signaling pathways (e.g., over-activation of myc transcription and inhibition of NOTCH signaling), which is entirely independent from a classification based on anatomical tumor type (classified as pancreatic tumor, breast ductal tumor, etc.).

Figure 7:
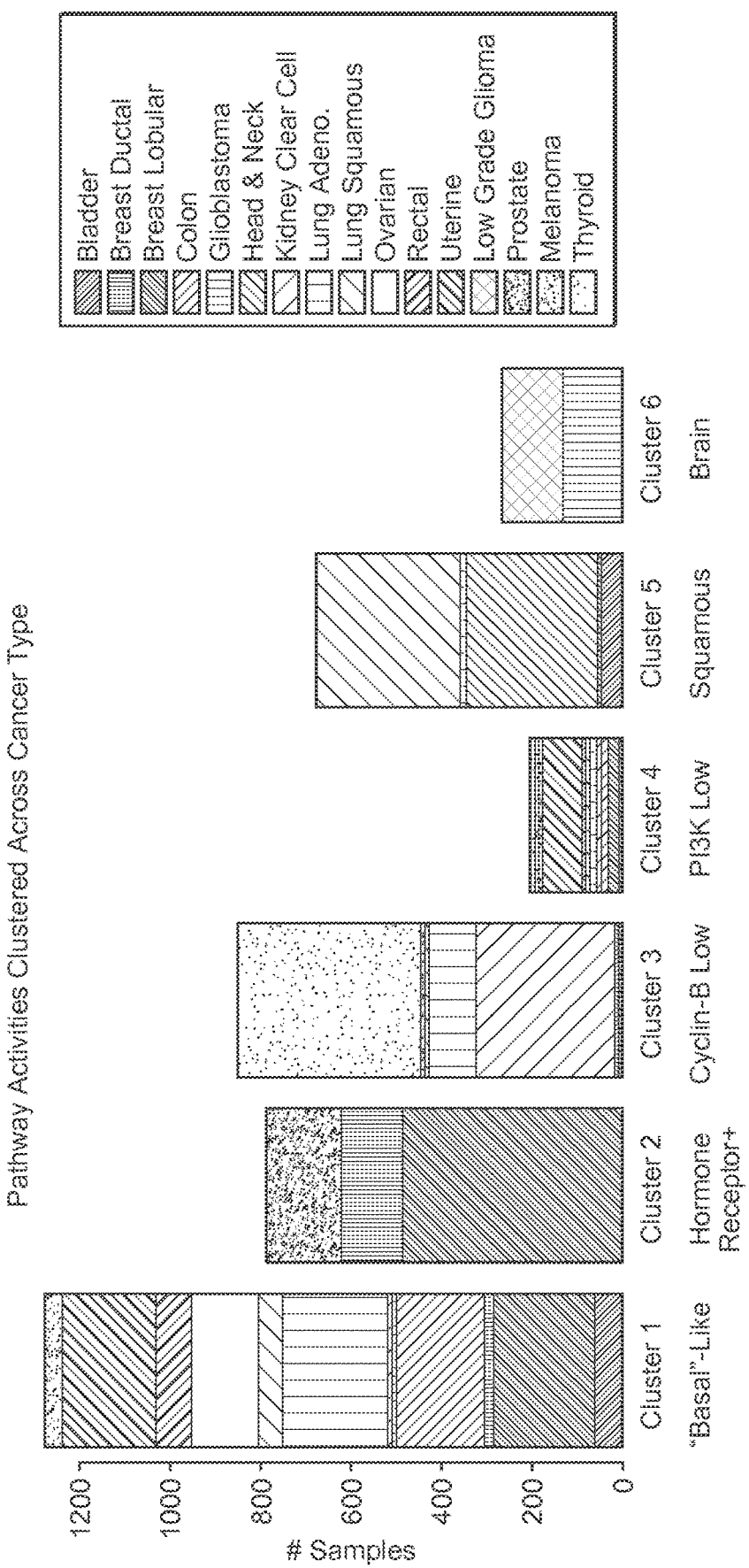
FIG. 7 is a graph depicting pathway activities clustered across various tumor types.

FIG. 7 exemplarily illustrates a different perspective of the findings of FIG. 6 where the tumor classification is expressed as clusters per FIG. 6. Here, it is readily apparent that entirely unrelated tumors (e.g., uterine, rectal, lung adeno.) can be classified according to specific signaling pathways characteristics having specific molecular signatures. For example, the molecular signature may comprise information about one or more pathway elements within a pathway (e.g., Ras, Raf, MEK, Myc). As such, where a tumor shares a common pathway characteristic with one or more common molecular signatures with another unrelated tumor, the tumor may in fact be treatable using treatment modalities know for the unrelated tumor. Most typically, the molecular signature information may include a drug identification (e.g., where Ras is mutated and overexpressed, drug information may include suitable Ras inhibitors) and/or a type of interaction with the one or more pathway elements (e.g., where Hec1 is mutated and overactive, drug information may include suitable Hec1/Nek inhibitors). Therefore, and viewed from another perspective, a patient tumor may be characterized as belonging to a specific class where that class is defined as having unrelated and distinct members (tumors) sharing common pathway characteristics/molecular signatures within a pathway. Based on the so established classification, treatment options may be selected based on treatment options known or available for the unrelated and distinct members. It should be appreciated that the treatment option may target a mutated element of a particular pathway, but also that the treatment option may target a non-mutated element of another pathway that compensates for a defect in a pathway in which a mutated element is disposed.

Figure 8:
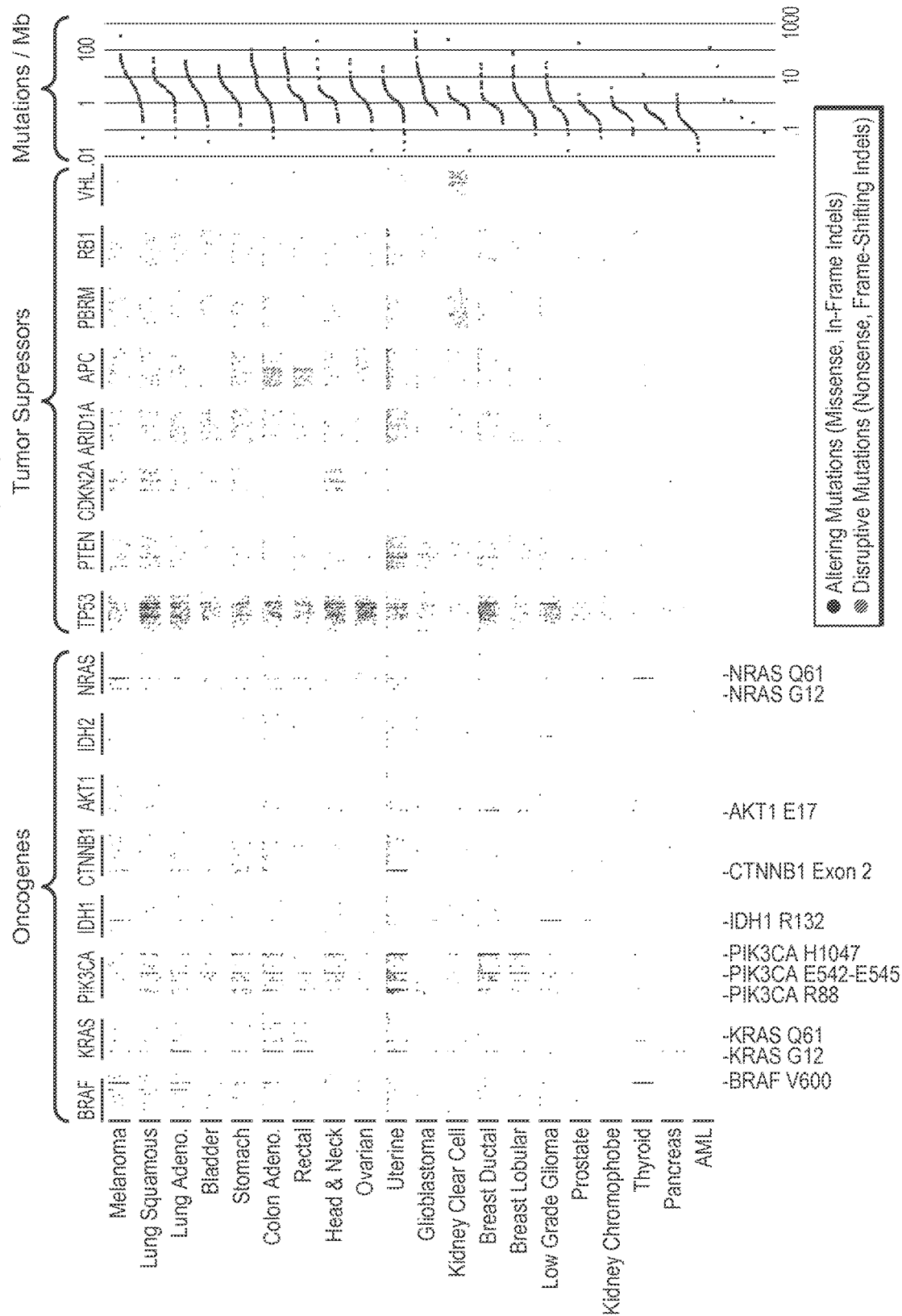
FIG. 8 is an exemplary graph depicting mutation distribution for various tumor types.

In another manner of classification, the inventors contemplate that selected pathways and/or pathway elements may be analyzed from a multiple different tumors as is exemplarily shown in FIG. 8. Here, selected pathway elements (e.g., tumor suppressors and oncogenes) are plotted against different tumors, which provides a rapid identification of shared pathway characteristics and molecular signatures common to multiple tumors. For example, the KRAS G12 mutant is associated with uterine, rectal, and colon cancers, while mutated APC is associated with colon adenocarcinoma and rectal cancers.

Therefore, the inventors contemplate that a patient record will typically include one or more treatment recommendations based on the molecular signature of the tumor cells (and with that based on the shared pathway characteristics with other unrelated tumors). In other words, a treatment recommendation for a first patient with a first tumor may be based on a shared pathway characteristics with a second patient with a distinct second tumor.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Moreover, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Moreover, all methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer-assisted method of treating a cancer patient by identifying a molecular signature for a tumor cell, comprising:
   receiving a plurality of data sets from a respective plurality of patients, wherein at least two of the plurality of patients are diagnosed with first and second tumors, respectively, wherein the first and second tumors are different anatomical tumors that originate from different anatomical organs of the patients; wherein each data set is representative of genomics information from tumor and matched normal cells;
   receiving transcriptomics information for the at least two patients;
   identifying shared pathway characteristics among the tumor cells of the first and second different anatomical tumors using the genomics information and the transcriptomics information;
   assigning, on the basis of the shared pathway characteristics, a molecular signature to the tumor cells of the first and second different anatomical tumors, wherein the molecular signature is assigned independently of an anatomical tumor type;
   identifying a shared molecular signature between the first and second tumors, wherein the shared molecular signature comprises a shared pathway element between the first and second tumors that is a druggable target; and
   treating the cancer patient having the second tumor with a treatment that is known effective to treat the first tumor, wherein the treatment targets the shared pathway element, wherein the shared pathway element is a mutated pathway element, and the treatment targets the shared pathway element by targeting another pathway element that compensates for a defect of the mutated pathway element.

2. The method of claim 1, wherein the plurality of data sets are in a BAMBAM format, a SAMBAM format, a FASTQ format, or a FASTA format.

3. The method of claim 1, wherein the plurality of data sets are BAMBAM diff objects.

4. The method of claim 1, wherein the plurality of data sets comprise mutation information, copy number information, insertion information, deletion information, orientation information and/or breakpoint information.

5. The method of claim 1, wherein at least three of the plurality of patients are diagnosed with different anatomical tumors.

6. The method of claim 1, wherein at least five of the plurality of patients are diagnosed with different anatomical tumors.

7. The method of claim 1, wherein the genomics information is whole genome sequencing information.

8. The method of claim 1, wherein the genomics information is exome sequencing information.

9. The method of claim 1, wherein the transcriptomics information comprises information on transcription level.

10. The method of claim 1, wherein the transcriptomics information comprises information on RNA sequence.

11. The method of claim 1, wherein the transcriptomics information covers at least 50% of all exomes in the genomics information from the tumor cells.

12. The method of claim 1, wherein the transcriptomics information covers at least 80% of all exomes in the genomics information from the tumor cells.

13. The method of claim 1, wherein the shared pathway characteristics are selected from the group consisting of a constitutively activated pathway, a functionally impaired pathway, and a dysregulated pathway.

14. The method of claim 1, wherein the shared pathway characteristics are characterized by a mutated non-functional protein, mutated dysfunctional protein, an overexpressed protein, or an underexpressed protein in a pathway.

15. The method of claim 1, wherein the transcriptomics information is used in the step of identifying shared pathway characteristics to infer reduced or absence of function of a protein encoded by a mutated gene.

16. The method of claim 1, wherein the step of identifying shared pathway characteristics is performed using a probabilistic pathway model.

17. The method of claim 1, wherein compensating for a defect of the mutated pathway element comprises inhibiting a function of the mutated pathway.

18. The method of claim 17, wherein the information of the molecular signature comprises drug identification and type of interaction with the one or more pathway elements.

19. The method of claim 1, further comprising updating or generating a patient record using the shared molecular signature.

* * * * *